United States Patent
Synowicki et al.

(10) Patent No.: US 7,187,443 B1
(45) Date of Patent: *Mar. 6, 2007

(54) METHOD OF DETERMINING BULK REFRACTIVE INDICIES OF LIQUIDS FROM THIN FILMS THEREOF

(75) Inventors: Ronald A. Synowicki, Lincoln, NE (US); Thomas E. Tiwald, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 448 days.

This patent is subject to a terminal disclaimer.

(21) Appl. No.: 10/824,555

(22) Filed: Apr. 14, 2004

Related U.S. Application Data

(63) Continuation-in-part of application No. 10/407,578, filed on Apr. 7, 2003, now Pat. No. 6,738,139.

(60) Provisional application No. 60/405,845, filed on Aug. 26, 2002.

(51) Int. Cl.
*G01J 4/00* (2006.01)
(52) U.S. Cl. ..................................................... 356/369
(58) Field of Classification Search ............... None
See application file for complete search history.

(56) References Cited

U.S. PATENT DOCUMENTS

| | | | | |
|---|---|---|---|---|
| 3,973,994 A | | 8/1976 | Redfield ....................... 136/89 |
| 3,985,447 A | * | 10/1976 | Aspnes ........................ 356/118 |
| 4,514,582 A | * | 4/1985 | Tiedje et al. ................ 136/256 |
| 4,590,574 A | * | 5/1986 | Edmonds et al. ........... 364/498 |
| 4,683,160 A | * | 7/1987 | Bloch et al. ................. 428/141 |
| 5,107,105 A | * | 4/1992 | Isobe et al. .................. 250/225 |
| 5,420,680 A | * | 5/1995 | Isobe et al. .................. 365/128 |
| 5,502,560 A | * | 3/1996 | Anderson et al. ........... 356/128 |
| 5,610,708 A | * | 3/1997 | Anderson et al. ........... 356/128 |
| 5,910,842 A | * | 6/1999 | Piwonka-Corle et al. ... 356/369 |
| 6,392,756 B1 | * | 5/2002 | Li et al. ...................... 356/369 |
| 6,444,898 B1 | * | 9/2002 | Fujisawa et al. ............ 136/256 |
| 6,639,673 B1 | * | 10/2003 | Freund et al. ............... 356/369 |
| 6,738,139 B1 | * | 5/2004 | Synowicki et al. ......... 356/369 |
| 6,930,835 B2 | * | 8/2005 | Mearini et al. ............. 359/582 |
| 2002/0003665 A1 | * | 1/2002 | Mearini et al. ............. 359/586 |
| 2003/0025899 A1 | * | 2/2003 | Amara et al. ............... 356/128 |

* cited by examiner

*Primary Examiner*—Gregory J. Tooley, Jr.
*Assistant Examiner*—Juan Valentin, II
(74) *Attorney, Agent, or Firm*—James D. Welch

(57) ABSTRACT

Disclosed is a method for determination of bulk refractive indicies of flowable liquids utilizing thin films thereof on a roughened surface of a rigid or semi-rigid object.

16 Claims, 4 Drawing Sheets

US 7,187,443 B1

METHOD OF DETERMINING BULK REFRACTIVE INDICIES OF LIQUIDS FROM THIN FILMS THEREOF

The application is a CIP of application Ser. No. 10/407,578 Filed Apr. 7, 2003 now U.S. Pat. No. 6,738,139, and therevia Claims Benefit from Provisional Application Ser. No. 60/405,845 Filed Aug. 26, 2002.

TECHNICAL FIELD

The disclosed invention relates to methodology for determination of bulk refractive indicies of liquids, and more specifically to determination of bulk refractive indicies of liquids utilizing thin films thereof which have viscosity low enough to flow easily onto a roughened surface, which viscosity remains low during, and after practice of the present invention metholgy.

BACKGROUND

It is known to determine the refractive indicies of bulk fluids utilizing Ellipsometry, Polarimetry, or Intensity techniques. Briefly, a beam of electromagnetism is caused to interact with a contained volume of said fluid and the resulting changes therein is monitored, said changes being related to the refractive index. Where Ellipsometry or Polarimetry are utilized, the electromagnetic beam is polarized.

A problem can develop where the fluid is a liquid at room temperature, the volume of liquid is limited and/or the container for the liquid interacts with the liquid and effects or masks desired results. Further, where a bulk liquid is contained in an open surface container, said container must be maintained in an upright position and aligned with respect to the effect of gravity, to prevent liquid spillage therefrom.

The disclosed invention recognizes the identified problem and provides a solution in the form of providing a means for presenting a liquid which makes even very thin films thereof appear as optically think films.

A Search of patents was conducted with the disclosed invention in mind, the results of which follow.

Patents cited by the Examiner during prosecution of the CoPending patent application Ser. No. 10/407,578 are:

Published Patent Application No. US2002/0003665 A1 of Mearini et al., describes depositing Diamond Like Carbon (DLC) onto a roughened surface to cause it to become functionally smooth. While use of an Ellipsometer is contemplated to monitor the process, it is noted that DLC is not a liquid, and nothing in said 665 application suggests replacing the DLC with a liquid.

Published Patent Application No. US2003/0025899 A1 of Amara et al., describes a method and apparatus for determining refractive index and thickness of thin films.

U.S. Pat. No. 6,392,756 to Li et al., which describes method and apparatus for determining physical properties of thin films deposited on a complex substrate.

U.S. Pat. No. 4,683,160 to Bloch et al., which describes solar cells with correlated roughness substrate.

U.S. Pat. No. 5,910,842 to Piwonka-Corle et al., describes a focused bean ellipsometer.

U.S. Pat. No. 6,444,898 to Fujisawa et al., describes a transparent layer product on a glass article.

Continuing, while not obviating of the disclosed invention, probably the best prior art identified are U.S. Pat. Nos. 5,502,560 and 5,610,708 to Anderson et al., which describe apparatus comprising a diffraction grating, and methodology of its use in determining concentrations of materials in fluids. An element comprising a diffraction grating is placed into contact with a sample and a beam of polarized light is caused to pass through said element and reflect from the interface between said diffraction grating and the sample. The reflected spectrum is reported to have features related to the complex dielectric constant, which is dependent on concentrations of materials in the sample.

U.S. Pat. Nos. 5,307,105 and 5,420,680 to Isobe et al. describe apparatus and methodology for measuring refractive index and thickness of a thin film formed on a substrate.

U.S. Pat. No. 4,590,574 to Edmonds et al. describes a method for determining oxygen and carbon in a silicon substrate having a rough surface.

U.S. Pat. No. 4,514,582 to Tiedje et al. describes a system which enhances optical absorption in amorphous silicon comprising a substrate with a sandblasted surface, upon which is deposited a thin film of semiconductor.

U.S. Pat. No. 3,985,447 to Aspnes is disclosed as it describes measurement of thickness and refractive index of a thin film on a substrate.

U.S. Pat. No. 3,973,994 to Redfield describes a solar cell comprising a thin layer of active semiconductor on the surface of a transparent substrate which has grooves present in the back side thereof.

Even in view of the prior art, need exists for a method which allows measurement of bulk refractive indicies of a liquid using only a small amount thereof.

DISCLOSURE OF THE INVENTION

The disclosed invention is a method for measuring the bulk refractive index of flowable liquids utilizing thin films thereof, and can be practiced with said thin film surface oriented facing either laterally or vertically or at an in-between angle. Known procedures for alignment of solid samples can be utilized as a result of the provided simulated solid sample comprising a two sided, typically substantially flat rigid or semi-rigid object, one side thereof being roughened and having the flowable liquid applied thereupon. Said surface roughening can be achieved by a variety of techniques, including common mechanical grinding or jet-spraying of abrasives onto a surface of a two sided, typically substantially flat rigid or semi-rigid object made of for instance, dielectric, (glass or polymer), metal, semiconductor or paper. Periodic re-wetting can become necessary, however, where an absorbent material such as paper is utilized. Also, providing a quantity of flowable liquid to said roughened side can be achieved by any functional approach such as simple dripping thereonto, by spraying, painting or daubing. It is noted that low or high viscosity flowable liquids, including gels, epoxies, photoresists and the like can be investigated utilizing the disclosed invention methodology, and that while flowable liquids adhere to and conform to a roughened surface at the interface therebetween, an outer surface thereof is smooth and suitable for investigating by specular optical measurements using electromagnetic beams. Specular effects entered by the roughened surface have been found to be minimal. Further, even where flowable liquids containing surfactants which eliminate tension adsorption effects, a thin film of flowable liquid on said roughened surface of said two sided rigid or semi-rigid object can be oriented even vertically during investigation with an electromagnetic beam, as thin films of flowable liquid adhere well to roughened surfaces and flow only extremely slowly.

The disclosed invention can be recited as a method of determining bulk refractive indices of flowable liquids comprises the steps of:

in any functional order practicing steps a, b and c:
 a) providing a quantity of flowable liquid;
 b) providing a rigid or semi-rigid object comprising two sides which is roughened on one side thereof;
 c) providing a source means of electromagnetic radiation, a sample supporting stage and detector means;
 d) covering the roughened side of said rigid or semi-rigid object, with a thin film of said flowable liquid;
 e) placing said rigid or semi-rigid object which has been covered with a thin film of said flowable liquid on said roughed side thereof, onto the sample supporting stage with said thin film of flowable liquid being directly accessible;
 f) causing said source means of electromagnetic radiation to provide a beam of electromagnetic radiation and directing it to be incident on and reflect from said thin film of flowable liquid on said roughened side of said rigid or semi-rigid object, and then enter said detector means such that it produces an output in response thereto;
 g) analyzing resulting detector means output to the end that bulk refractive indicies of the thin film of flowable liquid are determined.

The step of providing a rigid or semi-rigid object can further involve roughening a second side thereof.

Said method of determining the bulk refractive indices of flowable liquids can involve orienting the thin film of flowable liquid on said roughened side of said rigid or semi-rigid object is oriented to face in a direction selected from the group consisting of:
 upward or downward;
 laterally; and
 in a direction between facing vertically and laterally.

Another recitation of a disclosed invention method of determining bulk refractive indices of flowable liquids comprises the steps of:

in any functional order practicing steps a, b and c:
 a) providing a quantity of flowable liquid;
 b) providing a rigid or semi-rigid object comprising two sides which is roughened on at least one side thereof;
 c) providing an ellipsometer or polarimeter system which comprises:
  source means of electromagnetic radiation:
  polarizer means;
  sample supporting stage;
  analyzer means;
  detector means;
 d) covering the roughened side of said rigid or semi-rigid object, with a thin film of said flowable liquid;
 e) placing said rigid or semi-rigid object which has been covered with a thin film of said flowable liquid on said roughed side thereof, onto the sample supporting stage of said ellipsometer system with said thin film of flowable liquid being directly accessible;
 f) causing said ellipsometer or polarimeter system source means of electromagnetic radiation to provide a beam of electromagnetic radiation and directing it to pass through said polarizer, be incident on and reflect from said thin film of flowable liquid on said roughened side of said rigid or semi-rigid object, pass through said analyzer and then enter said detector means such that it produces an output in response thereto;
 g) analyzing resulting detector means output to the end that bulk refractive indicies of the thin film of flowable liquid are determined.

Again, the step of providing a rigid or semi-rigid object can further involve roughening a second side thereof.

And again, said method of determining the bulk refractive indices of flowable liquids can involve orienting the thin film of flowable liquid on said roughened side of said rigid or semi-rigid object is oriented to face in a direction selected from the group consisting of:
 upward or downward;
 laterally; and
 in a direction between facing vertically and laterally.

The disclosed invention can be recited as a method of determining bulk refractive indices of flowable liquids comprising providing a two sided, typically substantially flat rigid or semi-rigid object which has been roughened on at least one side thereof, and providing a quantity of flowable liquid to said roughened side, followed by causing a source means of electromagnetic radiation to provide a beam of electromagnetic radiation and directing it to interact with said flowable liquid coated substantially flat roughened surface of said two sided substantially flat rigid or semi-rigid object, such that it specularly reflects from the thin film of said flowable liquid and then enters a detector, and such that the detector produces an output in response thereto. Performing an analysis of the detector output enables determination of bulk flowable liquid refractive indicies.

The disclosed invention can alternatively be recited as a method of determining bulk refractive indices of flowable liquids comprising utilizing an ellipsometer system which comprises:
 source means of electromagnetic radiation:
 polarizer means;
 sample supporting stage;
 analyzer means;
 detector means.

Said method comprises providing a two sided substantially flat rigid or semi-rigid object which has been roughened on at least one side thereof, and providing a quantity of flowable liquid to said roughened side. It has been found that causing said ellipsometer system source means of electromagnetic radiation to provide a beam of electromagnetic radiation and directing it to pass through said polarizer, be incident upon said flowable liquid coated substantially flat roughened surface of said two sided substantially flat rigid or semi-rigid object, such that it reflects from the thin film of said flowable liquid, passes through said analyzer and then enters said detector, and such that the detector produces an output in response thereto, enables performing an analysis of the detector output which enables determination of bulk flowable liquid refractive indicies.

Benefits of the presently disclosed invention include elimination of ripples which result from external vibrations when volumes of flowable liquid are subjected investigated, in addition to enabling easy alignment. In addition, as the flowable liquid adheres well to the roughened surface, it can be held in place for extended periods of time, even where low viscosity flowable liquids are investigated.

The disclosed invention can be practiced utilizing electromagnetic wavelengths in any range, including NIR, IR, Visual, UV etc., as long as the average roughness dimension is much greater than is the wavelength. Where this is the case a surface which appears rough at a given wavelength will also appear rough at nearby wavelengths. Reflections of electromagnetic radiation which enters the thin film and interacts with the roughened surface and make it to a detector have been found to be negligible, thereby making the thin film appear a infinitely thick. That this is the case is verified by measuring refractive indicies of both a thin film and a bulk volume of the same flowable liquid, and obtaining the same result.

The disclosed invention can be practiced with any flowable liquid which functionally adheres to a roughened surface, but as a non-limiting example of a flowable liquid, it is noted that water is a flowable liquid with viscosity in a range of:

| DEGREES F | CENTIPOISE |
|---|---|
| 32 | 1.794 |
| 40 | 1.546 |
| 50 | 1.310 |
| 60 | 1.129 |
| 70 | 0.982 |
| 80 | 0.862 |
| 90 | 0.764 |
| 100 | 0.682 |
| 120 | 0.559 |
| 140 | 0.470 |
| 160 | 0.401 |
| 180 | 0.347 |
| 200 | 0.305 |

NOTE: at 20 degrees Centigrade another reference reports water has a viscosity of 1.00 centipoise.

Viscosities for other non-limiting examples of liquids, at 70 degrees Fahrenheit, which can be applied under the teachings of the present invention are listed below:

| DEGREES F | CENTIPOISE |
|---|---|
| Kerosene | 2.05 |
| #2 Fuel Oil | 5.92 |
| #4 Fuel Oil | 12.6 |
| Transformer Oil | 16.2 |
| Hydraulic Oil | 34.6 |
| SAE 10W Oil | 52.2 |
| SAE 10 Oil | 88.0 |
| SAE 20 Oil | 173 |
| SAE 30 Oil | 352 |
| SAE 50 Oil | 880 |
| SAE 60–70 Oil | 1760 |
| Molasses | 8800–17,300 |

Other non-limiting examples of liquids which might be applied in practice of the present invention are:

Ethyl Alcohol which has a viscosity of 16 centipoise at 20 degrees Centigrade;

Glycerin which has a viscosity of 830 to 1490 centipoise at 20 degrees Centigrade;

Heavy Machine oil which has a viscosity of 660 centipoise at 15 degrees Centigrade and 127.4 centipoise at 37.8 degrees Centigrade;

Light Machine oil which has a viscosity of 113 centipoise at 15 degrees Centigrade and a viscosity of 4.9 centipoise at 100 degrees Centigrade;

Mercury which has a viscosity of 1.55 centipoise at 20 degrees Centigrade;

Fomblin YL-VAC Fluid which has a viscosity of 276 cST at 20 degrees Centigrade and 10.6 cST at 100 degrees Centigrade;

Torrlub Vacum Grease which has a viscosity of 495 cST at 38 degrees Centigrade and 98 cST at 43 degrees Centigrade;

Water which has a viscosity of 1.00 centipoise at 20 degrees Centigrade;

The upper limit of temperature is that at which the substrate with the roughened surface melts, or the liquid evaporates; and the lower limit is that at which the liquid changes phase to a solid, such as by freezing.

In general, the terminology "flowable liquid", as used herein, means that practice of said method does not result in a non-flowable liquid. The method is characterized in that the flowable liquid is flowable before, during, and remains so after practice thereof.

The method can also involve the known practice of roughening the second side of the two sided substantially flat rigid or semi-rigid object to prevent backside reflections. This is typically necessary only where the refractive index of the roughened surface, in an important wavelength range, is very close to that of the flowable liquid and electromagnetic radiation can reflect from said back surface and exit the flowable liquid surface in a way that interferes with the electromagnetic radiation which reflects directly from said flowable liquid surface.

The disclosed invention will be better understood by reference to the Detailed Description Section of this Specification in conjunction with reference to the Drawings.

SUMMARY OF THE INVENTION

It is therefore a purpose and/or objective of the disclosed invention to teach a method of utilizing small volume thin films of flowable liquid to determine a bulk refractive index thereof.

Other purposes and/or objectives of the disclosed invention will become apparent by a reading of the Specification and Claims.

DETAILED DESCRIPTION

Figure 1:
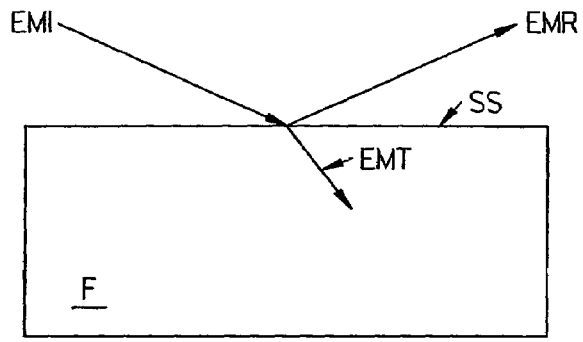
FIG. 1 demonstrates a prior art approach to determining bulk refractive indicies.

Turning now to the Drawings, FIG. 1 demonstrates a prior art approach to determining bulk refractive indicies. An incident electromagnetic beam (EMI) reflects from the smooth top surface (SS) of the effectively infinitely deep volume of flowable liquid (F) as reflected electromagnetic beam (EMR). Any transmitted electromagnetic beam (EMT) can not reflect back out thereof as no functional backside of the flowable liquid (F) is available to effect reflection. That is, the volume of flowable liquid (F) provided is sufficient to be effectively infinitely deep.

Figure 2:
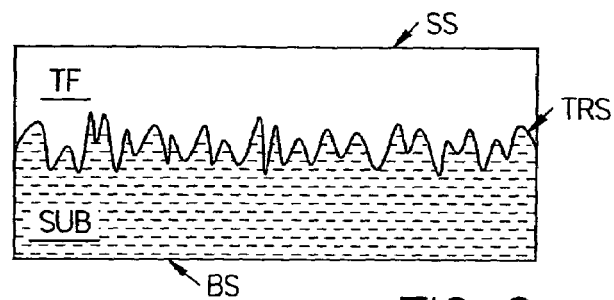
FIG. 2 shows a two sided substantially flat rigid or semi-rigid object, with a thin film of flowable liquid on a roughened top side thereof.

FIG. 2 shows a disclosed invention two sided substantially flat rigid or semi-rigid object (SUB), with a smooth upper surfaced thin film (TF) of flowable liquid present on a roughened top side (TRS) thereof.

Figure 3:
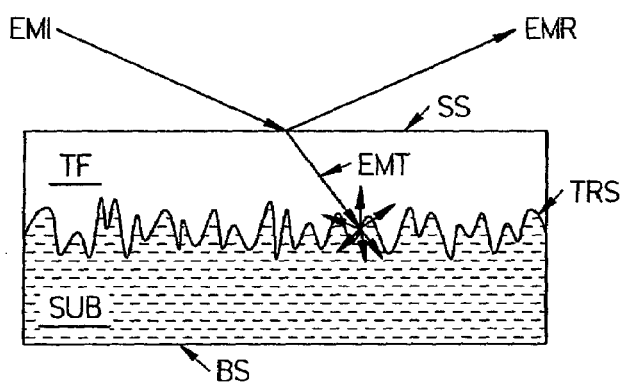
FIG. 3 demonstrates a disclosed invention approach to determining bulk refractive indicies, including indication of application of electromagnetic radiation thereto.

FIG. 3 demonstrates a disclosed invention approach to determining bulk refractive indicies utilizing only a thin film (TF) thereof, including indication of application of incident (EMI), and resulting smooth top surface (SS) reflected (EMR) and transmitted (EMT) electromagnetic radiation components. Note that transmitted (EMT) electromagnetic radiation is dispersed at the roughened top surface (TRS) and does not reflect in a way that interferes with the reflected (EMR) electromagnetic radiation.

Figure 4:
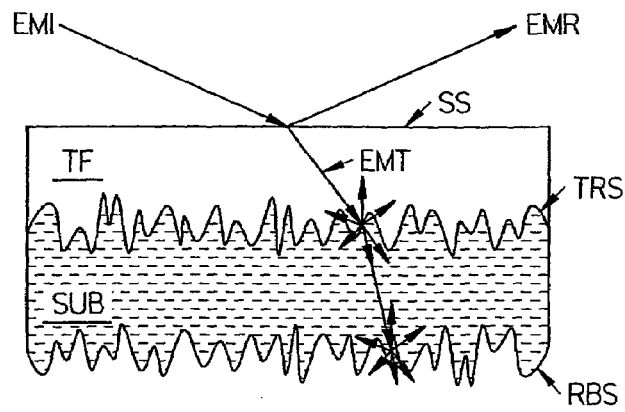
FIG. 4 demonstrates a disclosed invention approach to determining bulk refractive indicies wherein both sides of the two sided substantially flat rigid or semi-rigid object are roughened, including indication of application of electromagnetic radiation thereto.

FIG. 4 demonstrates a disclosed invention approach to determining bulk refractive indicies as in FIG. 3, but also shows the bottom side (RBS) of the two sided substantially flat rigid or semi-rigid object (SUB) is also roughened. Incident (EMI), and resulting top surface reflected (EMR) and transmitted (EMT) electromagnetic radiation components are again shown, along with dispersal of the transmitted electromagnetic beam where it interacts with the bottom roughened surface (RBS).

Figure 5:
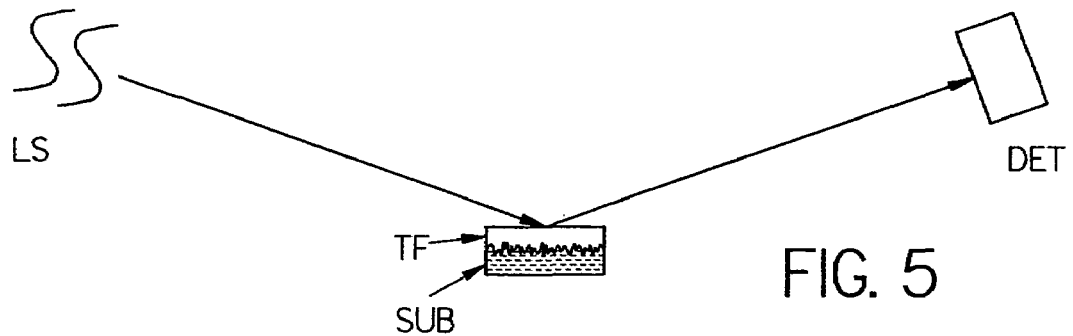
FIG. 5 shows an exemplary system for providing and detecting non-polarized electromagnetic radiation which is caused to interact with a two sided substantially flat rigid or semi-rigid object, at least the upper surface thereof being roughened.

FIG. 5 shows an exemplary system for providing and detecting non-polarized electromagnetic radiation which is caused to interact with a two sided substantially flat rigid or semi-rigid object (SUB), at least the upper surface thereof being roughened and to which is applied a thin film of flowable liquid (TF). Shown are a source means (LS) of electromagnetic radiation, and a Detector (DET) and incident (EMI) and reflected (EMR) beams.

Figure 6:
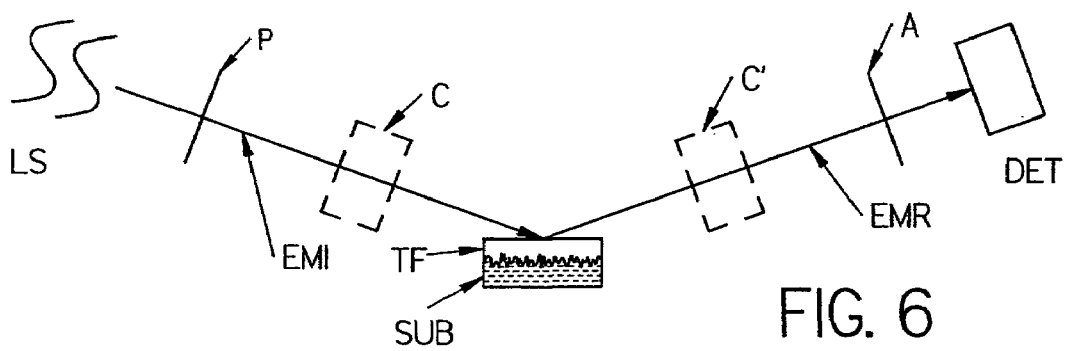
FIG. 6 shows an exemplary system for providing and detecting polarized electromagnetic radiation which is caused to interact with a two sided substantially flat rigid or semi-rigid object, at least the upper surface thereof being roughened.

FIG. 6 shows an exemplary system for providing and detecting polarized electromagnetic radiation which is caused to interact with a thin film of flowable liquid (TF) present on a two sided substantially flat rigid or semi-rigid object (SUB) with a roughened upper surface. FIG. 6 is much as FIG. 5 but with added polarizer (P), analyzer (A) and optional compensators (C) (C').

Figure 7:
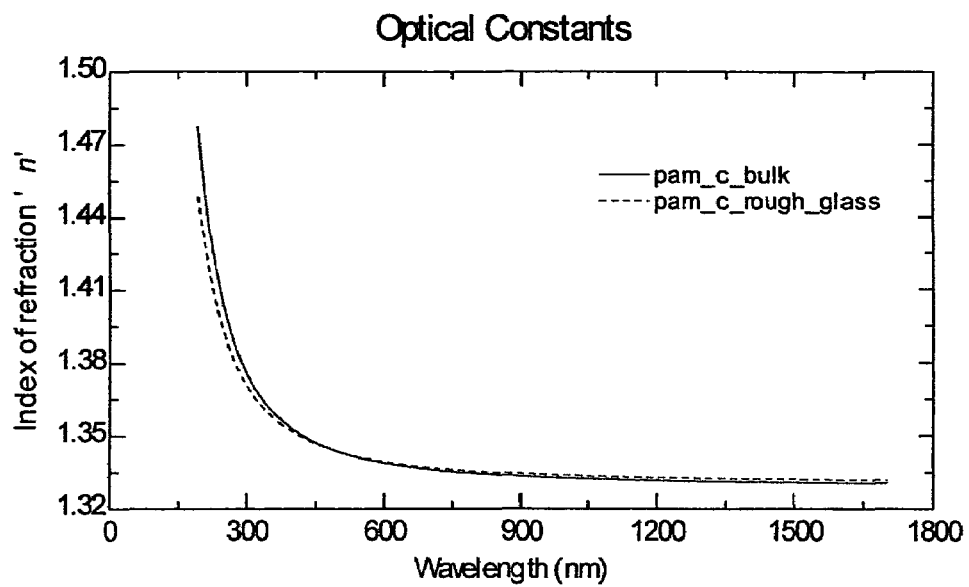
FIG. 7 demonstrates exemplary comparative experimental refractive index results determined both by conventional investigation of a bulk sample of PAM Cooking Surfactant, and by disclosed invention investigation of a thin film thereof.

FIG. 7 demonstrates exemplary comparative experimental refractive index results determined both by conventional investigation of a bulk sample of PAM Cooking Surfactant, and by disclosed invention investigation of a thin film thereof over a wide range, (ie 290–1700 nm), of wavelengths. Note the particularly good results between about 450–1700 nm. It is disclosed that a J.A. Woollam CO. M2000 (Registered Trademark), Spectroscopic Ellipsometer was used to obtain the data which when analyzed provided the results.

Figure 8:
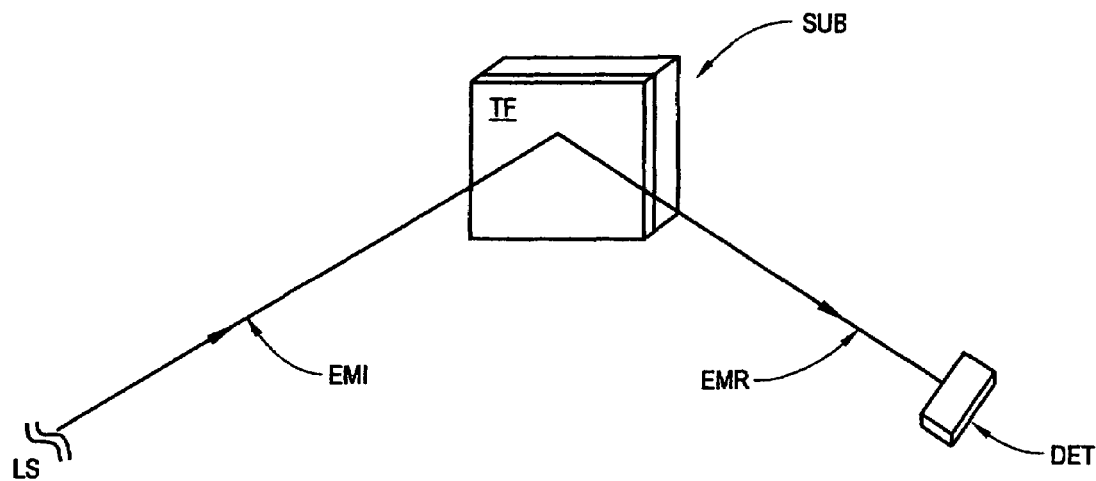
FIG. 8 is similar to FIG. 5, but shows the rigid or semi-rigid object oriented to face laterally.
Figure 9:
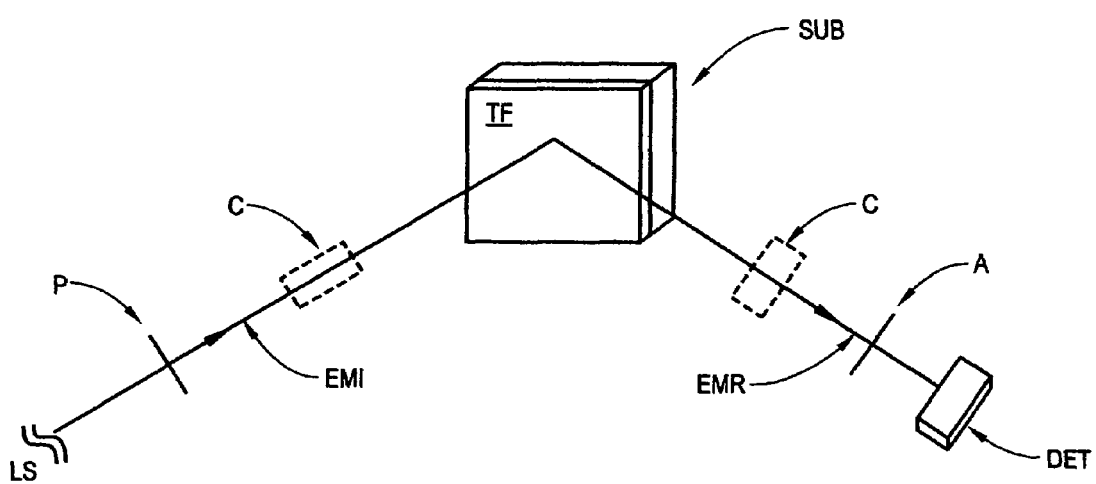
FIG. 9 is similar to FIG. 6, but shows the rigid or semi-rigid object oriented to face laterally.
Figure 10:
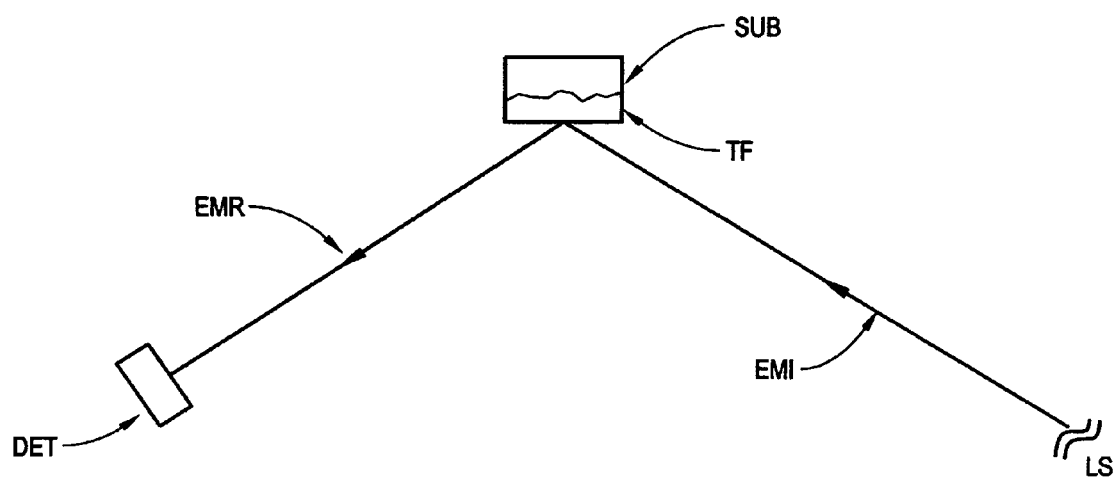
FIG. 10 shows the rigid or semi-rigid object (SUB), as described with respect to FIG. 5 oriented to downward.
Figure 11:
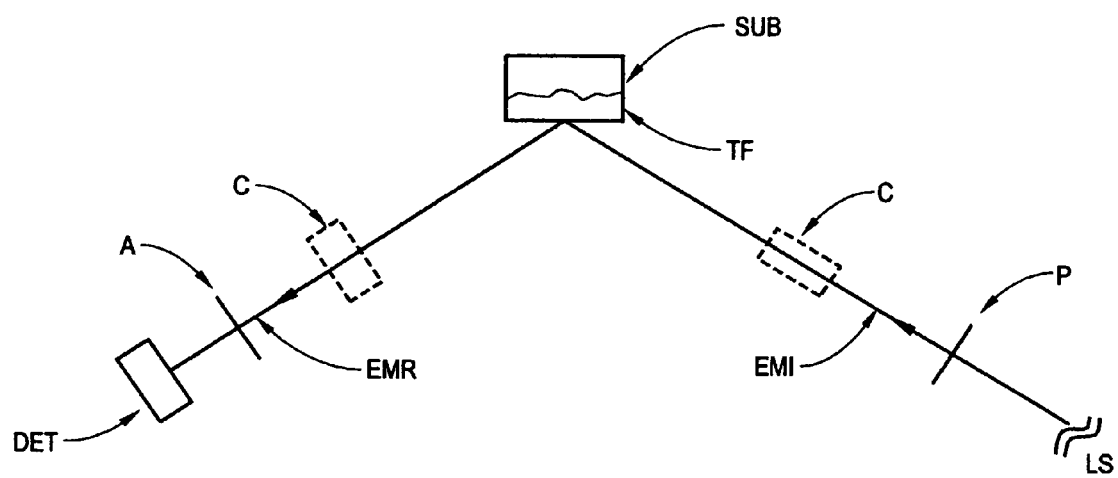
FIG. 11 shows the rigid or semi-rigid object (SUB), as described with respect to FIG. 6 oriented to downward.

FIGS. 8 and 9 are included to show the rigid or semi-rigid object (SUB), as described with respect to FIGS. 5 and 6, oriented to face laterally. FIGS. 10 and 11 show the rigid or semi-rigid object (SUB), as described with respect to FIGS. 5 and 6, oriented to downward.

Note, the terminology "top" and "bottom" in the foregoing were utilized only to coordinate with the Drawings. A disclosed invention can be utilized with the two sided substantially flat rigid or semi-rigid object (SUB) in any orientation, such that the surface of the thin flowable liquid (TF) faces in any direction.

It is noted that the term "flowable liquid" as used in this Specification functionally refers to a fluid which is flowable before the method of disclosed invention is applied, during application thereof and remains so after application thereof. Generally, liquids have viscosities in the range of 0.1 to 10,000 centipoise over a temperature range of 100.0 to 0.0 degrees Centigrade are within the definition of the term "flowable liquid" as it is used in this Specification. Further, a "flowable liquid", as the term is used in this Specification, has a viscosity which does not substantially change because the disclosed method is applied thereto, or because the flowable liquid is selected to become non-flowable after application thereof, (eg. such as where DLC is deposited on a roughened surface of a substrate when said DLC is in a fluid flowable state, but where said DLC hardens once in place). In addition, it is noted that the terminology "flowable" indicates that like, for instance water or motor oil or even molasses, if placed on an incline the liquid will move theredown. This is distinguished over Diamond Like Carbon (DLC) which once deposited while in a fluid state becomes a solid, and thereafter does not flow down the substrate upon which it is deposited it said substrate is placed on the incline.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of determining bulk refractive indices of flowable liquids comprising the steps of:

in any functional order practicing steps a, b and c:
  a) providing a quantity of flowable liquid;
  b) providing a rigid or semi-rigid object comprising two sides which is roughened on one side thereof;
  c) providing a source means of electromagnetic radiation, a sample supporting stage and detector means;
  d) covering the roughened side of said rigid or semi-rigid object, with a thin film of said flowable liquid;
  e) placing said rigid or semi-rigid object which has been covered with a thin film of said flowable liquid on said roughed side thereof, onto the sample supporting stage with said thin film of flowable liquid being directly accessible;
  f) causing said source means of electromagnetic radiation to provide a beam of electromagnetic radiation and directing it to be incident upon and reflect from said thin film of flowable liquid on said roughened side of said rigid or semi-rigid object, and then enter said detector means such that it produces an output in response thereto;

g) analyzing resulting detector means output to the end that bulk refractive indicies of the thin film of flowable liquid are determined; and h) displaying the bulk refractive indicies determined in step g;

said method being characterized in that the flowable liquid is flowable before, during, and remains so after practice thereof.

2. A method as in claim 1, in which the step of providing a rigid or semi-rigid object comprising two sides further involves roughening a second side thereof.

3. A method of determining the bulk refractive indices of flowable liquids as in claim 1, in which the thin film of flowable liquid on said roughened side of said rigid or semi-rigid object is oriented to face in a direction selected from the group consisting of:

upward or downward;
laterally; and
in a direction between facing vertically and laterally.

4. A method of determining the bulk refractive indices of flowable liquids as in claim 1, in which the thin film of flowable liquid on said roughened side of said rigid or semi-rigid object is oriented to face laterally.

5. A method of determining the bulk refractive indices of flowable liquids as in claim 1, in which the viscosity of the flowable liquid is within a range of 0.01 to 17,000 centipoise, both before and after practice of said method.

6. A method of determining the bulk refractive indices of flowable liquids as in claim 1, in which the viscosity of the flowable liquid is within a range of 0.01 to 17,000 centipoise, both before and after practice of said method; and in which the thin film of flowable liquid on said roughened side of said rigid or semi-rigid object is oriented to face laterally.

7. A method of determining the bulk refractive indices of flowable liquids as in claim 1, in which the low and high temperature range limits are where the thin film of flowable liquid on said roughened side of said rigid or semi-rigid object freezes and evaporates or the object melts.

8. A method of determining the bulk refractive indices of flowable liquids as in claim 1, in which the thin film of flowable liquid on said roughened side of said rigid or semi-rigid object is oriented to face up or down.

9. A method of determining bulk refractive indices of flowable liquids comprising the steps of:

in any functional order practicing steps a, b and c:
a) providing a quantity of flowable liquid;
b) providing a rigid or semi-rigid object comprising two sides which is roughened on at least one side thereof;
c) providing an ellipsometer or polarimeter system which comprises:
source means of electromagnetic radiation:
polarizer means;
sample supporting stage;
analyzer means;
detector means;
d) covering the roughened side of said rigid or semi-rigid object, with a thin film of said flowable liquid;

e) placing said rigid or semi-rigid object which has been covered with a thin film of said flowable liquid on said roughed side thereof, onto the sample supporting stage of said ellipsometer system with said thin film of flowable liquid being directly accessible;

f) causing said ellipsometer or polarimeter system source means of electromagnetic radiation to provide a beam of electromagnetic radiation and directing it to pass through said polarizer, be incident upon and reflect from said thin film of flowable liquid on said roughened side of said rigid or semi-rigid object, pass through said analyzer and then enter said detector means such that it produces an output in response thereto;

g) analyzing resulting detector means output to the end that bulk refractive indicies of the thin film of flowable liquid are determined; and h) displaying the bulk refractive indicies determined in step g;

said method being characterized in that the flowable liquid is flowable before, during, and remains so after practice thereof.

10. A method as in claim 9, in which the step of providing a rigid or semi-rigid object comprising two sides further involves roughening a second side thereof.

11. A method of determining the bulk refractive indices of flowable liquids as in claim 9, in which the thin film of flowable liquid on said roughened side of said rigid or semi-rigid object is oriented to face in a direction selected from the group consisting of:

upward or downward;
laterally; and
in a direction between facing vertically and laterally.

12. A method of determining the bulk refractive indices of flowable liquids as in claim 9, in which the thin film of flowable liquid on said roughened side of said rigid or semi-rigid object is oriented to face laterally.

13. A method of determining the bulk refractive indices of flowable liquids as in claim 9, in which the thin film of flowable liquid on said roughened side of said rigid or semi-rigid object is oriented to face up or down.

14. A method of determining the bulk refractive indices of flowable liquids as in claim 9, in which the viscosity of the flowable liquid is within a range of 0.01 to 17,000 centipoise, both before and after practice of said method; and in which the thin film of flowable liquid on said roughened side of said rigid or semi-rigid object is oriented to face laterally.

15. A method of determining the bulk refractive indices of flowable liquids as in claim 9, in which the low and high temperature range limits are where the thin film of flowable liquid on said roughened side of said rigid or semi-rigid object freezes and evaporates or the object melts.

16. A method of determining the bulk refractive indices of flowable liquids as in claim 9, in which the thin film of flowable liquid on said roughened side of said rigid or semi-rigid object is oriented to face up or down.

\* \* \* \* \*